United States Patent [19]

Bridgman

[11] 3,955,579
[45] May 11, 1976

[54] VACUUM CURET

[76] Inventor: Henry Bridgman, c/o Bridgman & Co. P.O. Box 71, Convent Station, N.J. 07961

[22] Filed: July 23, 1973

[21] Appl. No.: 381,740

[52] U.S. Cl. .............................. 128/304; 128/276
[51] Int. Cl.² ......................................... A61B 17/22
[58] Field of Search ........................... 128/276, 304

[56] References Cited
UNITED STATES PATENTS

| | | |
|---|---|---|
| 605,052 | 5/1898 | Cook ........................ 128/304 UX |
| 3,542,031 | 11/1970 | Taylor .............................. 128/304 |
| 3,661,144 | 5/1972 | Jensen et al. ....................... 128/304 |
| 3,749,090 | 7/1973 | Stewart ............................. 128/276 |
| 3,769,980 | 11/1973 | Karman ............................. 128/304 |
| 3,774,612 | 11/1973 | Marco .............................. 128/304 |
| 3,774,613 | 11/1973 | Woods, Jr. et al. ................. 128/304 |

Primary Examiner—Channing L. Pace
Attorney, Agent, or Firm—Roland Plottel

[57] ABSTRACT

A vacuum curet of novel design having a central portion which is tapered and an internal lumen which is preferably also tapered. This provides a curet which is rigid over its central and proximal end (i.e. the end that fits into a vacuum source) and maximal flexibility and small external diameter at its distal end portion. Further advantages of this arrangement are reducing the possibility of perforation (due to the flexibility of the distal end portion), better "feel" (due to the rigidity of the central and proximal end portion), and decreased trauma due to the thin wall thickness of the proximal end portion and a corresponding reduction in outside diameter for a given or required lumen diameter. The lumen of this design may also be mass produced. In an additional embodiment, there is a novel design on the tip openings at the distal end, which further minimizes the possibility of perforation.

10 Claims, 3 Drawing Figures

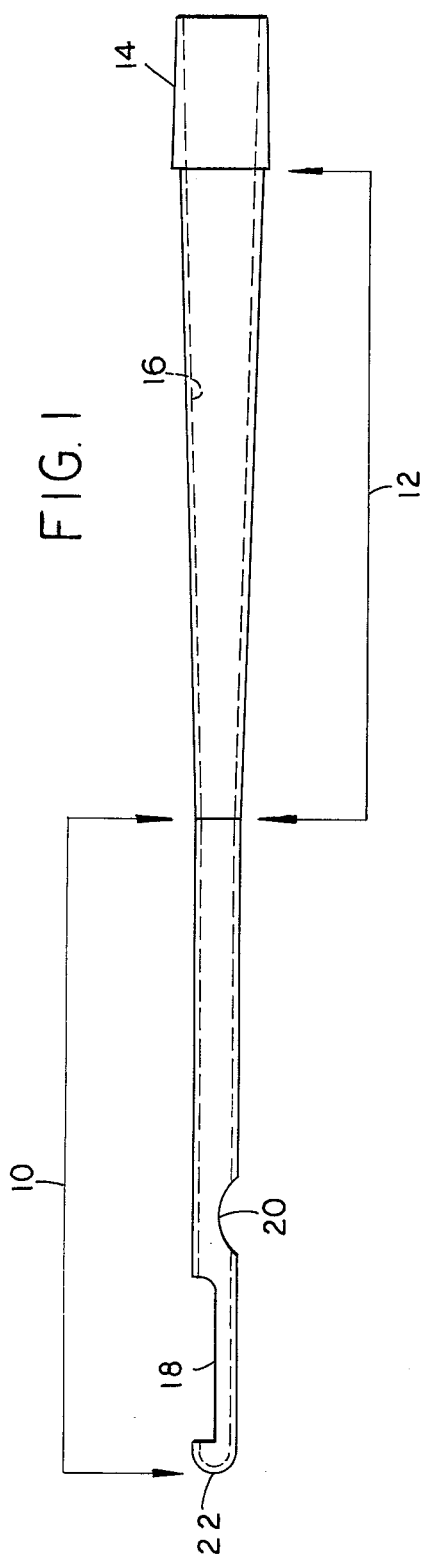
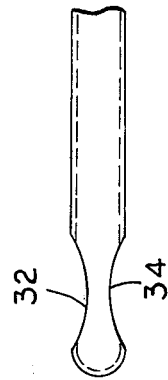
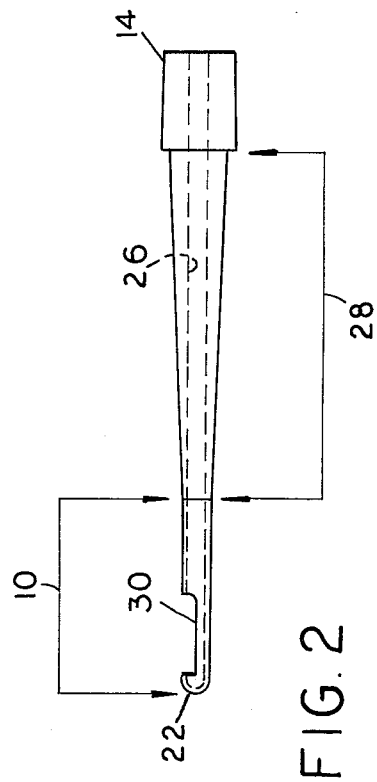

VACUUM CURET

The invention relates generally to medical and surgical apparatus and particularly to vacuum curets.

Curets have been used for many years to remove fluids and/or tissue from the body. A typical curet is a hollow tube having openings at each end. One opening is attached to a source of vacuum, typically by a hose. The opposite end is introduced into that portion of the body from which fluid and/or tissue is to be removed. When the vacuum is applied, the fluids and/or tissue are removed through the hollow portion of the curet.

Examples of typical applications for vacuum curet procedures (vacuum curettage) includes (1) diagnostic, e.g. collecting tissue for endometrial diagnostics, such as polyps, atypia, or adenocarcinoma; (2) surgical, e.g. abortions during the early months of pregnancy; and (3) menstrual regulation.

Examples or prior art curets and surgical apparatus using these curets are shown and described in my U.S. Pat. No. 3,713,444 — entitled Collection Bottle, and my co-pending U.S. Pat. application Ser. No. 258,960, filed on June 2, 1972, entitled Medical Aspiration System and Method. Reference may be made to those applications for illustrations of typical vacuum curettage procedures and complete vacuum curettage apparatus.

Curets have heretofore been made of stainless steel, bone and different plastics. If the curet is too rigid, there is the possibility, and the statistically observed fact, of undersirably piercing a membrane or wall in the body during a vacuum curettage procedure. If not rigid enough, the surgeon has difficulty in "feeling" what he is doing, and, where tissue is sampled, may not provide enough strength or leverage to obtain suitable specimens.

A specific example might be helpful. In uterine aspiration, the typical curet is 8 to 10 inches long. One end of the curet — which is attached to a source of suction and an adjacent intermediate portion which resides in the relatively wide vagina during the procedure — should be rigid. The other end of the curet — which is in the very narrow cervical canal protruding into the uterus during the procedure — should be (1) flexible to minimize the undesired possible perforation of the wall and (2) of a small diameter as possible to minimize the trauma associated with the cervix dilation. This diameter is determined by the procedure which dictates what the inside diameter, or flowthrough portion, of the curet must be. For certain procedures a minimum of 3½mm are needed. For others, 10mm may be needed. The only way to decrease the outer diameter of the curet is to make its walls as thin as possible over that portion in the cervical canal, and wider and more rigid in the intermediate and proximal portions, where size is not essential and more rigidity is needed. Prior art curets have not recognized this need, nor offered the solution of the present invention.

A second example illustrates a further aspect of the present invention: In the diagnostis sampling of endometrial tissue by a vacuum curettage, it is necessary that the aperture at the tip of the curet near the endometrial region have a sharp or cutting edge. This suggests a rigid curet. The curet itself must also be rigid enough to give the surgeon a feel as he moves the cutting tip of the curet over the endometrial surface. The curet, however, should also be flexible so as to avoid punching through the uterine wall. In the present invention, these problems have been identified and a novel tip opening and novel curet is provided which offers a solution thereto.

A difficulty heretofore attendant with prior art curets during vacuum curettage, especially in tissue sampling, was to reduce unnecessary blood loss and trauma to the sampling region and cervical canal. The curet of the present invention tends to minimize this blood loss and trauma.

A further aspect of the curet of the present invention is that it may be easily machine mass produced. Prior art curets of small internal diameter lumens were not capable of such manufacture. The curet of the present invention may be inexpensively mass produced and thus employed on a once-use-throw-away basis.

FIG. 1 is a plane view, not to scale, of one embodiment of the invention.

FIG. 2 is a plane view, not to scale, of an alternative embodiment of the invention.

FIG. 3, is a plane view, not to scale, of a portion of the distal end portion of a curet showing an alternative embodiment of the tip opening.

Referring now to FIG. 1, there is shown a plane view of the curet, constructed in accordance with the invention. The curet is not drawn to scale, but is exaggerated in certain dimensions to point-up various features. The curet is described herein with specific illustrative dimensions; it should be understood that these dimensions are for purposes of illustration only, and variations may be made therein without departing from the scope and spirit of the invention.

The curet shown in FIG. 1 is typically 8 inches in length. It has a distal end portion, 10, which is about 3½ to 4½ inches in length; a tapered shank, 12, about 3½ inches and a proximal end portion, 14, about 1 inch long. A lumen or hollow portion of the curet is shown in phantom and bears legend 16. In the tip region of the distal end portion are a pair of tip openings, 18 and 20, positioned in opposition, i.e. on opposite sides of the curet wall, and displaced from one another. The former opening, 18, is a macerator and the latter, 20, is semiround. The macerator opening, 18, is located close to the tip and the rounded one, 20, is on the opposite side and positioned further from the end. The positioning of the two openings, and the design of a macerator and rounded openings have a number of advantageous consequences. The macerator assures proper scraping action, and both openings bring about rapid fluid and tissue removal. This rapid removal of loosened tissue by opening 18 is extremely important, as this tends to minimize blood loss and trauma. The opposed tip openings combined with the flexibility of the distal end portion and the rounded tip at 22, tend to minimize accidental perforation. If the curet is pressed too hard against the tissue, there is a tendency for the tip not to proceed and perforate, but to fold over at that portion of the curet between the two openings, 18 and 20.

The proximal end, 14, has a slight outside slope which is adapted to fit onto a hose connected to a source of vacuum or onto any other source of suction. Its diameter typically is 0.532 inches where it joins the tapered portion, 12, and slopes down to approximately 0.500 inches at its end. While a slope fitting is shown in this Figure, any other convenient or conventional fitting may be used which provides a suitable connection to a vacuum source.

The outside diameter of the distal end portion, 10, is dictated by the surgical procedure. Curets typically come in several sizes, the most common have outside diameters of 4mm, 6mm, 8mm and 10mm. In English units, this is roughly equivalent to 0.157, 0.236, 0.304 and 0.393 inches respectively. The outside taper of the tapered portion, 12, is partially determined by the diameter of the distal end portion, 10. Thus, for example, in a "4mm" curet, the tapered portion would have its outside diameter increase from approximately 0.157 inches where it joins the distal end portion, 10, to approximately 0.500 inch where it joins the proximal end portion. As shown in the drawings, there is a slight necking-in at the latter joint.

The lumen, 16, increases in diameter from the distal to proximal ends. For example, with a 4mm curet, the diameter of the lumen (1) near the distal tip is typically 0.100 inches; (2) where the distal end portion, 10, joins the tapered portion, 12, is typically 0.117 inches; and (3) at the other end of the tapered portion, 12, where it joins the proximal end portion, 14, is in the order of 0.300 to 0.400 inches. The wall thickness in the distal end portion, 10, is minimal, consistent with the material of the curet. This provides (1) flexibility, thus lessening possible unwanted perforation during a procedure and (2) minimal outside diameter with maximal internal lumen, with the resulting decreased trauma, which directly follows from the smallest possible outside diameter. The inside diameter, of course, being large enough to carry off the required amount of fluids and semisolids.

Over the tapered central portion there is not the requirement of reducing trauma and a small outside diameter is not essential, as this portion is typically, during uterine aspiration, in a large vaginal area, rather than in the narrow cervix. A certain rigidity moreover is important to enable the surgeon to have a good feel and to firmly control the distal end portion of the curet. This is achieved by increasing the thickness of the curet wall in the tapered portion. In the above example the wall thickness increases from 0.020 to approximately 0.100 inches.

The curet itself is preferrably made of moldable plastic, such as polyvinyl chloride, polyethelene or polyvinylcarbide. Alternatively, any convenient or conventional moldable plastic compatable for surgical use may be employed. The curet of the present invention may be molded in a single molding step, e.g. by injection molding. The increase in the lumen diameter from the distal end to the proximal end facilitates the use of this single-molding step, and specifically the stripping of the curet from the mold. With a lumen of constant internal diameter, it is difficult to use single molding techniques. The consequence of being able to use this manufacturing technique — one which lends itself to automation — is to greatly reduce the cost of manufacture.

Referring now to the drawing of FIG. 2, there is shown schemically, a curet similar to the curet of FIG. 1, however, whose lumen, 26, is of substantially constant diameter. It has a tapered shank, 28, and enjoys a flexible distal end portion with a more rigid tapered shank portion. It has only one opening, 30, at the distal end portion.

FIG. 3 is a schematic diagram of an alternative embodiment of the tip openings. Here there are two rounded tip openings, 32 and 34, in opposition to each other, but equally spaced from the end of the curet. The advantage of this arrangement is that the curet will tend to fold over at the end portion region, rather than be rigid enough to perforate through the uterine wall.

Variations may be made in the tip openings. For example — disposition of the openings; one, or more than two openings; and openings of different configurations.

The invention has been described with a specific example giving particular dimensions. It should be understood that these dimensions are for purposes of illustration only and various modifications may be made therefrom without departing from the scope and spirit of the invention.

I claim:

1. A vacuum curet comprising
   a tube of flexible material having a central lumen extending therethrough, a distal end portion adopted to be inserted into a body cavity, a proximal end portion adopted to be connected to a vacuum source, and an intermediate tapered shank;
   said distal end portion having a narrow predetermined, outside diameter; and means for curetting at its tip region; and
   means for providing greater rigidity in said tapered shank than in said distal end portion.

2. A curet according to claim 1, comprising at least a pair of openings at said distal end portion tip region in opposed relationship.

3. A curet according to claim 1, wherein said curetting means is a macerator.

4. A curet according to claim 1, wherein said curetting means includes a rounded opening.

5. A curet according to claim 2, wherein said curetting means includes a pair of tip openings one of which is a macerator, and the other is rounded; said macerator being closer to the end of said curet than said rounded tip openings.

6. A curet according to claim 1, wherein said greater rigidity is provided by a lumen substantially of a constant diameter and said tapered shank having an outside diameter increasing in size from said distal end portion to said proximal end portion.

7. A curet according to claim 1, wherein said lumen has a diameter which increases between the proximal and distal end portions.

8. A curet according to claim 7, wherein said lumen diameter also increases from said distal end region tip to said tapered shank.

9. A curet according to claim 1, wherein the greater rigidity is provided by the thickness of the wall in the tapered shank area which increases from the distal end portion to the proximal end portion.

10. A curet according to claim 1 wherein said distal end portion is closed at its tip end (22) and said flexible material is a single piece of molded plastic.

* * * * *